United States Patent
Rauchschwalbe et al.

(10) Patent No.: US 6,750,354 B2
(45) Date of Patent: Jun. 15, 2004

(54) PROCESS FOR THE ALKYLATION OF 3,4-DIHYDROXYTHIOPHENE-2,5-DICARBOXYLIC ESTERS

(75) Inventors: Günter Rauchschwalbe, Leverkusen (DE); Alexander Klausener, Pulheim (DE); Josef Bremen, Leverkusen (DE); Ralf-Ingo Schenkel, Düsseldorf (DE); Adolf Winkler, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 87 days.

(21) Appl. No.: 10/256,836

(22) Filed: Sep. 27, 2002

(65) Prior Publication Data

US 2003/0097007 A1 May 22, 2003

(30) Foreign Application Priority Data

Oct. 1, 2001 (DE) .......................................... 101 48 437

(51) Int. Cl.$^7$ ............................................. C07D 409/00
(52) U.S. Cl. ............................................. 549/60; 549/64
(58) Field of Search ..................................... 549/60, 64

(56) References Cited

U.S. PATENT DOCUMENTS

| | | | | |
|---|---|---|---|---|
| 5,111,327 A | * | 5/1992 | Blohm et al. ............... | 526/256 |
| 5,187,608 A | * | 2/1993 | Blohm et al. ............... | 359/273 |
| 6,084,108 A | * | 7/2000 | Fevig et al. .................. | 549/61 |
| 6,369,239 B2 | * | 4/2002 | Rauchschwalbe et al. .... | 549/50 |
| 6,503,643 B1 | * | 1/2003 | Heuer et al. ................. | 428/690 |

OTHER PUBLICATIONS

Polym. Mater. SCI 72, 1996, pp. 672–674, Balasubramanian Sankaran and John R. Reynolds, "Synthesis and Electrochemistry of Polydioxyethyienethiophene and its Alkyl Substituted Derivatives".

Synthetic Communictions, 26(11), 1996, pp. 2205–2212, M. Coffey et al, "A Facile Synthesis of 3,4–Dialkoxythiophenes".

Pei Q et al: "Electrochromic and highly stable poly (3, 4–ethylenedioxythiophene) switches between opaque blue-black and transparent sky blue" Polymer, Elsevier Science Publishers B.V. GB, Bd. 35, Nr. 7, 1994, Seiten 1347–1351, XP001025972, ISSN: 0032–3861 Seite 1348.

Schottland P et al: "Synthesis and Polymerization of new monomers derived from 3, 4–ethylenedioxythiophene" Journal de chimie physique, societe de chimie physique, Paris, Fr, Bd. 95, Nr. 6, 1998, Seiten 1258–1261, XP001013494, ISSN: 0021–7689, Seite 1260, Umsetzung von 4 zu 5.

Paquette, L. A. (Ed.): "Encyclopedia of Reagents of Organic Synthesis, Volume 7" J. Wiley & Sons, Chichester XP002216647 Seiten 4724–4725: Tetra–n–butylammonium Bromide, 1998.

Ber. Dt. Chem. Ges., 43, 1910, pp. 901–906, O. Hinsberg, "Synthetische Versuche mit Thiodiglykolsaureester".

Ber. Dt. Chem. Ges., 45, 1912, pp. 2413–2418, O. Hinsberg, "Über Thiopen–Und Furan–Derivate".

J. Prakt. Chem., 338, 1996, pp. 672–674, Andreas Merz and Christina Rehm, "Improved Preparation of 3,4–Dimethoxythiophene".

* cited by examiner

Primary Examiner—Deborah C. Lambkin
(74) Attorney, Agent, or Firm—Godfried R. Akorli; Diderico van Eyl

(57) ABSTRACT

The invention relates to a process for the alkylation of 3,4-dihydroxythiophene-2,5-dicarboxylic esters or their alkali metal or alkaline earth metal salts with alkylating agents in a polar diluent in the presence of quaternary onium salts.

15 Claims, No Drawings

PROCESS FOR THE ALKYLATION OF 3,4-DIHYDROXYTHIOPHENE-2,5-DICARBOXYLIC ESTERS

BACKGROUND OF THE INVENTION

1. Field of the Invention

The invention relates to a process for the alkylation of dihydroxythiophenedicarboxylic esters or their alkali metal or alkaline earth metal salts in the presence of organic onium salts.

2. Brief Description of the Prior Art 3,4-Dialkoxythiophenes and 3,4-alkylenedioxythiophenes are starting compounds for the preparation of electrically conductive polymers which may be transparent in thin layers and have recently been finding a wide range of uses. The polymers are used, for example, as electrodes, sensors, for producing capacitors or electroluminescent displays and other electro-optic components, for producing photovoltaic devices, as electrochromic layers, as auxiliaries for the production of metal coatings, as thin films for dissipating static charges, in gel electrolytes or in ion-exchange membranes. The properties of these polymers can be varied within wide limits by means of the length and the substitution pattern of the alkoxy or alkylene group. The polymers are generally prepared from the corresponding monomers by chemical or electrochemical methods. A particularly important 3,4-alkylenedioxythiophene is 3,4-ethylenedioxythiophene.

3,4-Dialkoxythiophenes and 3,4-alkylenedioxythiophenes are frequently prepared in a multistage synthesis from the corresponding 3,4-dialkoxythiophene-2,5-dicarboxylic acids and 3,4-alkylenedioxythiophene-2,5-dicarboxylic acids by decarboxylation. These acids are in turn prepared from the corresponding esters. 3,4-Dialkoxythiophene-2,5-dicarboxylic esters and 3,4-alkylenedioxythiophene-2,5-dicarboxylic esters can be prepared by alkylation of 3,4-dihydroxythiophene-2,5-dicarboxylic esters. While 3,4-dihydroxythiophene-2,5-dicarboxylic esters and their alkali metal and alkaline earth metal salts have for a long time been able to be obtained conveniently in good yield (cf. for example, O. Hinsberg, Ber. Dt. Chem. Ges. 43, 1910, 901–906 and 45, 1912, 2413–2418), their alkylation is in many cases difficult and able to be carried out only in moderate yields.

Merz et al., J. Prakt. Chem. 338, 1996, 672–674, describe the alkylation of 3,4-dihydroxythiophene-2,5-dicarboxylic esters which is carried out using dimethyl sulphate in toluene in the presence of the cation solvator [18]crown-6, giving a yield of free dicarboxylic acid of 73% of theory. However, a disadvantage of this process is the long reaction time of 48 hours. Furthermore, the starting material is used in the form of its dipotassium salt which has to be prepared separately from the diol. The alkylation using 1,2-dichloroethane as alkylating agent, which is said to lead to 3,4-ethylenedioxythiophene-2,5-dicarboxylic ester which is preferably used as starting material for preparing 3,4-ethylenedioxythiophene, was not able to be reproduced in the laboratory under the conditions stated.

M. Coffey et al., Synthetic Communications 26 (11), 1996, 2205–2212, describe the alkylation of 3,4-dihydroxythiophene-2,5-dicarboxylic esters in the form of the free diol by means of 1,2-dibromoethane in the presence of potassium carbonate at 150° C. in dimethylformamide. A disadvantage is the low yield of 52% of theory. In addition, the preparation of the free diol from the alkali metal salt initially obtained is an additional process step which has an adverse effect on the economics of the synthesis. A variant of this method in which the reaction temperature is 90° C. has been described by Sankaran and Reynolds, polym. Mater. SCI 72, 1995, 319–320.

There is therefore a need for a process for the alkylation of 3,4-dihydroxythiophene-2,5-dicarboxylic esters or their alkali metal or alkaline earth metal salts which is simple to carry out and gives good yields of the corresponding 3,4-dialkoxythiophene-2,5-dicarboxylic esters and 3,4-alkylenedioxythiophene-2,5-dicarboxylic esters at comparatively short reaction times.

SUMMARY OF THE INVENTION

We have now surprisingly found a process for the alkylation of compounds of the formula (I)

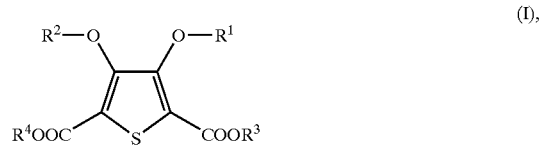

where
R$^1$ and R$^2$ are identical and are each hydrogen or are identical or different and are each an alkali metal or an alkaline earth metal and R$^3$ and R$^4$ are identical or different and are each a straight-chain or branched alkyl radical having from 1 to 10 carbon atoms, comprising reacting said compounds with alkylating agents in a polar diluent, wherein the reaction is carried out in the presence of quaternary onium salts of the formula (II)

where
A is nitrogen or phosphorus,
Y$^-$ is an anion and
R$^5$ to R$^8$ are identical or different and are each an alkyl radical having from 1 to 20 carbon atoms, an aryl radical having from 6 to 15 carbon atoms or an aralkyl radical having from 7 to 20 carbon atoms.

The process of the invention allows the alkylation of compounds of the formula (I) under mild conditions at low temperatures and short reaction times while giving excellent yields.

DETAILED DESCRIPTION OF THE INVENTION

In the process of the invention, preference is given to using compounds of the formula (I) in which R$^1$ and R$^2$ are identical or different and are each an alkali metal or an alkaline earth metal, for example lithium, sodium, potassium, rubidium, magnesium, calcium or strontium. They are obtained from the corresponding free 3,4-dihydroxythiophene-2,5-dicarboxylic esters by addition of alkali metal alkoxide or carbonate or alkaline earth metal alkoxide or carbonate or are obtained directly in the preparation of 3,4-dihydroxythiophene-2,5-dicarboxylic esters by reaction of thiodiacetic esters with oxalic esters in the presence of alkali metal alkoxide ("Hinsberg condensation"). Particular preference is given to using compounds of the formula (I) in which $R^1$ and $R^2$ are identical or different and are each an alkali metal, for example lithium, sodium, potassium or rubidium.

If compounds of the formula (I) in which $R^1$ and $R^2$ are different are used, then $R^1$ is particularly preferably sodium and R2 is particularly preferably potassium.

Very particular preference is given to using compounds of the formula (I) in which $R^1$ and $R^2$ are identical and are each lithium, sodium, potassium or rubidium, among which sodium and potassium are preferred.

The process of the invention is preferably carried out using compounds of the formula (I) in which $R^3$ and $R^4$ are identical or different and are each a straight-chain or branched alkyl radical having from 1 to 8 carbon atoms, particularly preferably a straight-chain or branched alkyl radical having from 1 to 6 carbon atoms, for example methyl, ethyl, n-propyl, isopropyl, n-butyl, sec-butyl, tert-butyl, n-pentyl, branched pentyls, n-hexyl, branched hexyls, 2-methylbutyl or 2-ethylbutyl.

If compounds of the formula (I) in which $R^3$ and $R^4$ are identical are used in the process of the invention, then $R^3$ and $R^4$ are each preferably methyl, ethyl, n-propyl, isopropyl, n-butyl, sec-butyl, tert-butyl, 2-methylbutyl or 2-ethylbutyl, particularly preferably methyl, ethyl, n-propyl or isopropyl, with the compounds mentioned being particularly preferably used in the form of their disodium or dipotassium salts ($R^1$ and $R^2$ are identical and are each sodium or potassium), very particularly preferably in the form of their disodium salt ($R^1$ and $R^2$ are identical and are each sodium). Very particular preference is given to using dimethyl 3,4-dihydroxythiophene-2,5-dicarboxylate in the form of its disodium salt.

In a preferred embodiment of the process of the invention, use is made of mixtures of compounds of the formula (I) as are obtained, for example, in the preparation of 3,4-dihydroxythiophene-2,5-dicarboxylic esters by reacting dibutyl thiodiacetate with diethyl oxalate in the presence of sodium methoxide in methanol ("Hinsberg condensation"). These are preferably mixtures in which $R^3$ and $R^4$ are identical or different and are each methyl, ethyl or butyl. Particular preference is given to using mixtures comprising dimethyl 3,4-dihydroxythiophene-2,5-dicarboxylate, methyl ethyl 3,4-dihydroxythiophene-2,5-dicarboxylate and methyl butyl 3,4-dihydroxythiophene-2,5-dicarboxylate. Very particular preference is given to using mixtures in the form of their salts ($R^1$ and $R^2$ are identical or different and are each an alkali metal or an alkaline earth metal), in which case particular preference is given to $R^1$ and $R^2$ being identical and each being sodium or potassium and very particular preference is given to $R^1$ and $R^2$ being identical and each being sodium. In a very particularly preferred embodiment, a mixture comprising the disodium salt of dimethyl 3,4-dihydroxythiophene-2,5-dicarboxylate, the disodium salt of methyl ethyl 3,4-dihydroxythiophene-2,5-dicarboxylate and the disodium salt of methyl butyl 3,4-dihydroxythiophene-2,5-dicarboxylate is used in the process of the invention.

The alkylating agents used in the process of the invention are customary alkylating agents known to those skilled in the art.

It is possible to use alkylating agents which contain only one leaving group and on reaction with the compounds of the formula (I) used in the process of the invention lead to compounds of the formula (III)

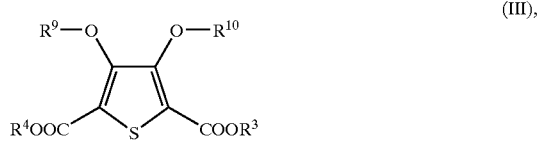

(III), where $R^9$ and $R^{10}$ are straight-chain or branched alkyl radicals which originate from the alkylating agent used in the particular case and $R^3$ and $R^4$ are as defined above.

Preference is here given to alkylating agents selected from the group consisting of alkyl halides, alkyl sulphates, alkyl methanesulphonates, alkyl benzene sulphonates and alkyl toluene sulphonates, preferably straight-chain or branched $C_1$–$C_8$-alkyl halides, sulphates, methane sulphonates, benzene sulphonates and toluene sulphonates. Particular preference is given to using alkyl halides, preferably straight-chain or branched $C_1$–$C_8$-alkyl halides, very particularly preferably straight-chain or branched $C_1$–$C_8$-alkyl chlorides or bromides, in particular dimethyl sulphate, methyl chloride, methyl bromide or methyl iodide.

Preference is given to using alkylating agents which contain two leaving groups and on reaction with the compounds of the formula (I) used in the process of the invention lead to compounds of the formula (IV)

(IV), where $R^{11}$ is a straight-chain or branched alkylene radical which originates from the alkylating agent used in the particular case and $R^3$ and $R^4$ are as defined above.

Preference is here given to using alkylating agents selected from the group consisting of alkyl dihalides, alkyl disulphates, alkyl dimethane sulphonates, alkyl dibenzene sulphonates and alkyl ditoluene sulphonates, preferably straight-chain or branched $C_1$–$C_8$-alkyl dihalides, disulphates, dimethane sulphonates, dibenzene sulphonates and ditoluene sulphonates. Particular preference is given to using alkyl dihalides, preferably straight-chain or branched $C_1$–$C_8$-alkyl dihalides, very particularly preferably straight-chain or branched $C_1$–$C_8$-alkyl dichlorides or dibromides, in particular 1,2-bis(mesyloxy)ethane, 1,2-dichloroethane, 1,2-dibromoethane and 1-bromo-2-chloroethane, among which very particular preference is given to 1,2-dichloroethane.

The alkylating agent used in the process of the invention is used in at least the stoichiometric amount; in general, it is advantageous to use an excess. Preference is given to using an excess of from 30 to 200 mol %, particularly preferably an excess of from 50 to 150 mol %, in particular an excess of from 70 to 100 mol %, based on the compounds of the formula (I).

The polar diluents used in the process of the invention are customary polar diluents known to those skilled in the art.

They can be used alone or in the form of mixtures. It is also possible to use polar diluents in the form of mixtures with nonpolar diluents.

Polar diluents used are preferably aprotic polar diluents selected from the group consisting of ethers, ketones, esters, amides, ureas, sulphoxides and sulphones, particularly preferably diethylene glycol dimethyl ether, dioxane, acetone, cyclohexanone, butyl acetate, N,N-dimethylformamide N-methylpyrrolidone, hexamethylphosphoramide, tetramethyl urea, dimethyl sulphoxide or tetramethylene sulphone (sulpholane).

The process of the invention is preferably carried out using quaternary onium salts of the formula (II) in which $Y^{31}$ is an anion selected from the group consisting of chloride, bromide, iodide, hydroxide, hydrogen sulphate, sulphate, methane sulphonate, toluene sulphonate and trifluoroacetate, particularly preferably chloride or bromide.

The process of the invention is preferably carried out using quaternary onium salts of the formula (II) in which $R^5$ to $R^8$ are identical or different and are each an alkyl radical having from 1 to 16 carbon atoms, an aryl radical having from 6 to 10 carbon atoms, for example phenyl or naphthyl, or an aralkyl radical having from 7 to 11 carbon atoms, for example benzyl, phenylmethyl or phenylethyl, particularly preferably methyl, ethyl, n-propyl, isopropyl, n-butyl, sec-butyl, tert-butyl, decyl, dodecyl, tetradecyl, phenyl or benzyl.

The process of the invention is particularly preferably carried out using quaternary onium salts of the formula (II) in which $R^5$ to $R^8$ are identical and are each an alkyl radical having from 1 to 6 carbon atoms, for example, methyl, ethyl, n-propyl, isopropyl, n-butyl, sec-butyl, tert-butyl, n-pentyl, branched pentyls, n-hexyl or branched hexyls, particularly preferably methyl, ethyl, n-propyl, isopropyl, n-butyl, sec-butyl or tert-butyl.

Very particular preference is given to using quaternary onium salts of the formula (II) selected from the group consisting of tetramethylammonium chloride, tetramethylammonium bromide, benzyldimethyltetradecyl-ammonium chloride, butyltriphenylphosphonium bromide, tetraphenylphosphonium bromide and tetrabutylphosphonium chloride in the process of the invention.

The quaternary onium salts of the formula (II) used in the process of the invention can be used individually or in the form of mixtures of various onium salts. Furthermore, they can be used as such or in the form of precursor compounds which are converted in situ into onium salts of the formula (II) under the conditions of the process of the invention, for example, tertiary amines or phosphines which are alkylated under the reaction conditions to form quaternary ammonium salts or phosphonium salts.

The onium salts used in the process of the invention are preferably used in a substoichiometric amount, preferably in an amount of from 1 to 20 mol %, based on dihydroxythiophene derivative (starting material), particularly preferably from 2 to 10 mol %, very particularly preferably in an amount of from 3 to 7 mol %, based on dihydroxythiophene derivative (starting material).

In a preferred embodiment, the process of the invention is carried out in the presence of an additional base, particularly preferably in the presence of alkali metal or alkaline earth metal carbonates, hydroxides, oxides or alkoxides, very particularly preferably in the presence of alkali metal carbonates, in particular sodium carbonate or potassium carbonate.

If an additional base is employed, it is preferably used in a substoichiometric to equivalent amount, preferably an amount of from 5 to 100 mol %, particularly preferably from 10 to 80 mol %, very particularly preferably from 25 to 50 mol %, based on the compounds of the formula (I).

The process of the invention is preferably carried out at a temperature of from 50 to 150° C. If 1,2-dichloroethane or 1,2-dibromoethane is used as alkylating agent, the process is preferably carried out at a temperature of from 100 to 140° C.

The process of the present invention is preferably carried out at atmospheric pressure or under superatmospheric pressure, preferably from 1 to 30 bar. Working under superatmospheric pressure permits the use of diluents whose boiling point at atmospheric pressure is significantly above the desired process temperature.

The process of the invention is preferably carried out by placing the diluent in a reaction vessel and adding preferably firstly compounds of the formula (I), quaternary onium salts of the formula (II) and preferably a base. The mixture is preferably brought to the desired reaction temperature and the alkylating agent is subsequently added, preferably dropwise. After the reaction is complete, compounds of the formula (III) or (IV) are obtained as products. These can be isolated and purified by pouring into water, filtration and recrystallization. In a preferred embodiment, these compounds are not isolated and purified. The compounds of the formula (III) or (IV) are, preferably after removal of at least part of the diluent, for example by distillation, hydrolysed to the corresponding carboxylic acids by methods known from the literature. These acids can, for example, be isolated by filtration or centrifugation after acidification of the reaction mixture.

In a particularly preferred embodiment of the process of the invention, 3,4-dihydroxy-2,5-thiophenedicarboxylic esters in the form of their salts, either individually or in the form of a mixture of various esters, are reacted with 1,2-dichloroethane and the resulting ester is hydrolysed to give 3,4-ethylenedioxythiophene-2,5-dicarboxylic acid in the form of a hitherto unknown, new monohydrate. Hitherto, 3,4-ethylenedioxythiophene-2,5-dicarboxylic acid has always been used as anhydrous compound obtained from the dihydrate by a separate drying step. However, the anhydrous compound is not stable on storage since it gradually attracts atmospheric moisture. The use of the new storage-stable monohydrate therefore has economic advantages.

The invention is further illustrated but is not intended to be limited by the following examples in which all parts and percentages are by weight unless otherwise specified.

EXAMPLES

Example 1

135 g of N,N-dimethylformamide were placed in a 1 liter stirred flask fitted with a reflux condenser. 55.2 g (0.2 mol) of dimethyl 3,4-dihydroxythiophene-2,5-dicarboxylate in the form of its disodium salt, 10.8 g of potassium carbonate and 3.4 g of tetrabutylammonium bromide were added thereto. The mixture was heated under nitrogen to a temperature of 130–135° C. As soon as the reaction temperature had been reached, 39 g (0.4 mol) of dichloroethane were added dropwise over a period of 15 minutes. After the dropwise addition was complete, the mixture was stirred for another 5 hours. The diluent was subsequently distilled off under reduced pressure (90% recovery of the diluent).

500 ml of water, 40 g of 2-propanol and 43 g of sodium hydroxide (45% strength aqueous solution) were then added, the reaction mixture was heated to 80° C. and stirred for 2 hours. The reaction mixture was subsequently acidified by dropwise addition of from 70 to 80 ml of HCl, which resulted in precipitation of the product. The precipitated product was filtered off with suction and washed three times with 90 ml each time of water. The moist product was dried in a vacuum drying oven (200 mbar/50° C.). This gave 38.5 g of 3,4-ethylenedioxythiophene-2,5-dicarboxylic acid in a purity of 91.9% (HPLC analysis), which corresponds to a yield of 76.9% of theory.

Comparative Example 1

The comparative example was carried out using a procedure analogous to Example 1, but without addition of tetrabutylammonium bromide. This resulted in a reaction time of 12 hours until conversion was complete (determined by HPLC analysis of samples taken at intervals). This gave 34.4 g of 3,4-ethylenedioxythiophene-2,5-dicarboxylic acid in a purity of 86.9% (HPLC analysis), which corresponds to a yield of 67% of theory.

Example 2

Example 2 was carried out using a method analogous to Example 1, using 0.177 mol of a mixture of dimethyl 3,4-dihydroxythiophene-2,5-dicarboxylate, methyl ethyl 3,4-dihydroxythiophene-2,5-dicarboxylate and methyl butyl 3,4-dihydroxythiophene-2,5-dicarboxylate (weight ratio 10:1:14) in the form of their disodium salts in place of the disodium salt of dimethyl 3,4-dihydroxythiophene-2,5-dicarboxylate.

3,4-Ethylenedioxythiophene-2,5-dicarboxylic acid was isolated in a yield of 76.8% of theory.

Examples 3 to 7

Examples 3 to 7 were carried out using a procedure analogous to Example 2, with the type of onium salt used being varied. The results are shown in Table 1.

TABLE 1

| Example No. | Onium salt | Amount [mol %] | Yield [% of theory] |
| --- | --- | --- | --- |
| 3 | Tetrabutylammonium chloride | 5 | 72 |
| 4 | Tetrabutylphosphonium bromide | 5 | 74 |
| 5 | Tetraphenylphosphonium bromide | 5 | 72 |
| 6 | Tetrabutylammonium chloride | 10 | 74 |
| 7 | Tetrabutylammonium chloride | 2 | 70 |

Example 8
Reaction Without Addition of Base 590 ml of N,N-dimethylformamide were placed in a stirred flask provided with a reflux condenser. 137.3 g (0.42 mol) of the ester mixture described in Example 2 and 8.1 g of tetrabutylammonium bromide were added thereto. The mixture was heated under nitrogen to a temperature of 80° C., and 96 g of 1,2-dichloroethane were then added dropwise and the reaction mixture was heated to 135° C. After the dropwise addition was complete, the mixture was stirred for another 5 hours. The diluent was subsequently distilled off under reduced pressure (26 mbar) at 80° C.

750 ml of water and 81.5 ml of sodium hydroxide (50% strength aqueous solution) were then added, the reaction mixture was heated to 98° C. and stirred for 5 hours. The reaction mixture was subsequently acidified to a pH of about 1 by dropwise addition of sulphuric acid, which resulted in precipitation of the product. The precipitated product was filtered off with suction and washed with a total of 1000 ml of water. The moist product was dried in a vacuum drying oven (200 mbar/50° C.).

This gave 3,4-ethylenedioxythiophene-2,5-dicarboxylic acid in a yield of 66% of theory.

Example 9

Example 9 was carried out using a procedure analogous to Example 2 but under pressure in an autoclave.

This gave 3,4-ethylenedioxythiophene-2,5-dicarboxylic acid in a yield of 74% of theory.

Example 10

455 ml of N,N-dimethylformamide were placed in a stirred flask provided with a reflux condenser. 186 g (0.569 mol) of the ester mixture described in Example 2, 22 g of tetrabutylammonium bromide and 35 g of potassium carbonate were added thereto. The mixture was heated under nitrogen to a temperature of 125° C., and 121 g of 1,2-dichloroethane were then added dropwise. After the dropwise addition was complete, the mixture was stirred for another 2 hours at 125° C. and for 1 hour at 135° C. The diluent was subsequently distilled off under reduced pressure (20 mbar) at 60° C. (recovery of the diluent >90%).

500 ml of water, 120 g of propanol and 120 g of sodium hydroxide (45% strength aqueous solution) were then added, and the reaction mixture was heated to 80–85° C. and stirred for 0.5 hours. Another 500 ml of water were subsequently added and the mixture was stirred for another 0.5 hours. To precipitate the reaction product, 234 ml of concentrated hydrochloric acid and 234 ml of water were placed in a vessel and heated to 50° C. The reaction mixture was added dropwise while stirring over a period of 4 hours. At the end of the dropwise addition, the pH was about 1 and the product precipitated. The mixture was cooled to 30° C. The precipitated product was quickly filtered off with suction and washed swiftly with water. The moist product was dried in a vacuum drying oven (100–200 mbar/50–60° C.).

This gave 107.2 g of 3,4-ethylenedioxythiophene-2,5-dicarboxylic acid in a purity of 92.5% (HPLC analysis), which corresponds to a yield of 75.7% of theory.

Example 11

The 3,4-ethylenedioxythiophene-2,5-dicarboxylic acid prepared as described in Example 1 was purified further by dissolution in aqueous sodium hydroxide, treatment with activated carbon and precipitation by means of hydrochloric acid.

Elemental analysis gave the following results:
C (found): 38.8%
H (found): 3.15%
S (found): 12.9%
C (calculated for monohydrate): 38.7%
H (calculated for monohydrate): 3.25%
S (calculated for monohydrate): 12.9%
C (calculated for anhydrous compound): 41.7%
H (calculated for anhydrous compound): 2.63%
S (calculated for anhydrous compound): 13.9%

Elemental analysis thus gives correct values for 3,4-ethylenedioxythiophene-2,5-dicarboxylic acid monohydrate. The water of crystallization can be removed by drying at 120° C.; the anhydrous product gradually attracts water again in moist air.

Example 12

600 ml of acetone were placed in a stirred flask provided with a reflux condenser. 248.5 g (0.9 mol) of dimethyl 3,4-dihydroxythiophene-2,5-dicarboxylate in the form of its disodium salt and 10 g of tetrabutylammonium bromide were added thereto. The mixture was heated to boiling and 600 g of dimethyl sulphate were added dropwise over a period of 4 hours. After the dropwise addition was complete, the mixture was stirred for another 2 hours. The reaction mixture was subsequently poured into 3 litres of water, and the solid which precipitated was filtered off with suction and washed with water. The moist product was dried in a vacuum drying oven (100 to 200 mbar/50 to 60° C.).

This gave 235 g of dimethyl 3,4-dimethoxythiophene-2,5-dicarboxylate in a yield of 85.5% of theory.

3,4-Dimethoxythiophene could be obtained by alkaline hydrolysis, decarboxylation and distillation.

Comparative Example 12

Comparative Example 12 was carried out using a procedure analogous to Example 12, but without addition of tetrabutylammonium bromide.

This gave 235 g of dimethyl 3,4-dimethoxythiophene-2,5-dicarboxylate in a yield of 65% of theory.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Process for alkylation compounds of the formula (I)

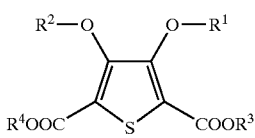

(I), where
R$^1$ and R$^2$ are identical and are each hydrogen or are identical or different and are each an alkali metal or an alkaline earth metal and
R$^3$ and R$^4$ are identical or different and are each a straight-chain or branched alkyl radical having from 1 to 10 carbon atoms,
comprising reacting said compounds with alkylating agents in a polar diluent, wherein the reaction is carried out in the presence of quaternary onium salts of the formula (II)

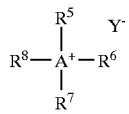

(II), where
A is nitrogen or phosphorus,
Y$^-$ is an anion and
R$^5$ to R$^8$ are identical or different and are each an alkyl radical having from 1 to 20 carbon atoms, an aryl radical having from 6 to 15 carbon atoms or an aralkyl radical having from 7 to 20 carbon atoms.

2. Process according to claim 1, wherein R$^1$ and R$^2$ are identical or different and are each an alkali metal or an alkaline earth metal and R$^3$ and R$^4$ are identical or different and are each a straight-chain or branched alkyl radical having from 1 to 8 carbon atoms.

3. Process according to claim 1 wherein R$^1$ and R$^2$ are identical and are each an alkali metal and R$^3$ and R$^4$ are identical or different and are each a straight-chain or branched alkyl radical having from 1 to 8 carbon atoms.

4. Process according to claim 1 wherein the compounds of formula (I) are dimethyl 3,4-dihydroxythiophene-2,5-dicarboxylate in the form of its disodium or dipotassium salt.

5. Process according to claim 1 wherein the compounds of formula (I) comprise mixtures of said compounds.

6. Process according to claim 5 wherein the mixtures comprise the disodium salt of dimethyl 3,4-dihydroxythiophene-2,5-dicarboxylate, the disodium salt of methyl ethyl 3,4-dihydroxythiophene-2,5-dicarboxylate and the disodium salt of methyl butyl 3,4-dihydroxythiophene-2,5-dicarboxylate.

7. Process according to claim 1 wherein the alkylating agents are selected from the group consisting of alkyl halides, alkyl sulphates, alkyl methane sulphonates, alkyl benzene sulphonates, alkyl toluene sulphonates, alkyl dihalides, alkyl disulphates, alkyl dimethane sulphonates, alkyl dibenzene sulphonates and alkyl ditoluene sulphonates.

8. Process according to claim 7 wherein the alkylating agents are selected from the group consisting of C$_1$–C$_8$-alkyl halides and C$_1$–C$_8$-alkyl dihalides.

9. Process according to claim 1 wherein the polar diluent is a polar aprotic diluent.

10. Process according to claim 9 wherein the polar aprotic diluent, is selected from the group consisting of ethers, ketones, esters, amides, ureas, sulphoxides and sulphones.

11. Process according claim 1 wherein the quaternary onium salts are of the formula (II) in which
A is nitrogen or phosphorus,
Y$^-$ is an anion selected from the group consisting of chloride, bromide, iodide, hydroxide, hydrogen sulphate, sulphate, methane sulphonate, toluene sulphonate and trifluoroacetate and
R$^5$ to R$^8$ are identical or different and are each an alkyl radical having from 1 to 16 carbon atoms, an aryl radical having from 6 to 10 carbon atoms or an aralkyl radical having from 7 to 11 carbon atoms.

12. Process according to claim 11 wherein the quaternary onium salt is selected from the group consisting of tetramethylammonium chloride, tetramethylammonium bromide, benzyldimethyltetradecylammonium chloride, butyltriphenylphosphonium bromide, tetraphenylphosphonium bromide and tetrabutylphosphonium chloride.

13. Process according to claim 1 wherein the reaction is carried out in the presence of an additional base.

14. Process according to claim 1 wherein the reaction is carried out at a temperature of from 50 to 150° C.

15. 3,4-Ethylenedioxythiophene-2,5-dicarboxylic acid monohydrate.

* * * * *